(12) United States Patent  (10) Patent No.: US 7,678,096 B2
Biddel et al.  (45) Date of Patent: Mar. 16, 2010

(54) CONNECTOR SYSTEM AND METHOD OF USING SAME

(75) Inventors: Christopher Biddel, Stonehouse (GB); Winfried Kuhlmann, Melsungen (DE); Colin Kalman Lanyi, Minchinhampton (GB); Oscar-Werner Reif, Hanover (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 422 days.

(21) Appl. No.: 11/410,185

(22) Filed: Apr. 24, 2006

(65) Prior Publication Data

US 2006/0252298 A1 Nov. 9, 2006

(30) Foreign Application Priority Data

May 3, 2005 (DE) .................... 10 2005 020 647

(51) Int. Cl.
*A61B 19/00* (2006.01)
*A61M 25/16* (2006.01)
*A61M 25/18* (2006.01)

(52) U.S. Cl. ...................... 604/403; 604/533

(58) Field of Classification Search ............... 604/4.01, 604/5.01, 6.01–6.16, 27, 28, 30, 32, 34, 40, 604/43, 153, 403–416, 533; 422/44–48; 606/192, 194; 137/625.12–625.14, 625.42–45, 137/597

See application file for complete search history.

(56) References Cited

U.S. PATENT DOCUMENTS

| 4,187,846 A | * | 2/1980 | Lolachi et al. ............... 604/411 |
| 6,565,525 B1 | * | 5/2003 | Burbank et al. .......... 604/93.01 |
| 2006/0079827 A1 | * | 4/2006 | Jensen et al. .................. 604/6.1 |

* cited by examiner

*Primary Examiner*—Leslie R. Deak
*Assistant Examiner*—Philip R Wiest
(74) *Attorney, Agent, or Firm*—Anthony J. Casella; Gerald E. Hespos (57) ABSTRACT

A connector system (10) for producing a sterile connection includes a fluid conduit (32), an engagement device (14, 22) designed to engage with a complementary engagement device (16, 24) of a complementary connector (12), a displacement device (26) with a substantially plane displacement surface (30) and a fluid conduit aperture (60) which extends through the displacement surface (30) and is connected to the fluid conduit (32), with the displacement device (26) being designed to displace the connector (12) and the complementary connector (12) relative to one another in a displacement direction (40) after the engagement device (14, 22) has engaged with the complementary engagement device (16, 24), and with the displacement direction (40) being substantially parallel to the displacement surface (30), and a sterile cover device (20, 74) designed to cover at least the fluid conduit aperture (60) in a sterile manner. The invention also relates to a method of use of the connector system (10) and of the complementary connector (12) for sterile connection of a fluid inlet of the connector (10) to a fluid outlet of the complementary connector.

15 Claims, 4 Drawing Sheets

CONNECTOR SYSTEM AND METHOD OF USING SAME

BACKGROUND OF THE INVENTION

1. Field of the Invention

The present invention relates to a connector system for leaktight connection of a fluid inlet of a connector to a fluid outlet of a complementary connector, and to the method of use of the connector and of the complementary connector for sterile connection of a fluid inlet of the connector to a fluid outlet of the complementary connector.

2. Description of the Related Art

A great many connectors have been developed, for example for handling biological fluids or liquids, such as blood plasma. It is important that the properties of the fluid remain unchanged as the fluid passes through the connectors. In particular, it is often necessary to protect the fluids from environmental effects, for example when the connectors are used in a nonsterile environment. After the connectors have been connected to one another, it is in most cases necessary to ensure that the fluid guided through the connectors is not exposed to any environmental effects and, in particular, is not contaminated. In other words, even though the connectors are being handled in a nonsterile environment, it is often necessary to ensure that a sterile connection is permitted between two connectors.

It is an object of the invention to permit a sterile connection in a simple manner. This object is achieved by the connector system of the subject invention and the method of use of the connector and of the complementary connector of the subject invention.

SUMMARY OF THE INVENTION

According to one aspect of the present invention, a connector system is made available for producing a sterile connection, with
 a fluid conduit,
 an engagement device designed to engage with a complementary engagement device of a complementary connector,
 a displacement device with a substantially plane displacement surface and a fluid conduit aperture which extends through the displacement surface and is connected to the fluid conduit,
  the displacement device being designed to displace the connector and the complementary connector relative to one another in a displacement direction after the engagement device has engaged with the complementary engagement device, and
  the displacement direction being substantially parallel to the displacement surface, and
 a sterile cover device designed to cover at least the fluid conduit aperture in a sterile manner.

The connector according to the present invention can be connected in a simple manner to a complementary connector and can, if appropriate, be detached from the latter again. It is in particular possible, according to the invention, to fix the connector on a complementary connector with the aid of the engagement device and the complementary engagement device. The connector can then be displaced relative to the complementary connector until the fluid conduit aperture of the connector and the fluid conduit aperture of the complementary connector lie substantially opposite one another, as a result of which a flow of fluid is permitted from the connector into the complementary connector. In particular, the displacement device allows the connector and the complementary connector to be displaced relative to one another along the displacement direction, it being possible for the displacement device to comprise guide devices, for example, via which the connector and the complementary connector can be displaced relative to one another, while each movement of the connector relative to the complementary connector in a direction different than the displacement direction is substantially prevented.

Advantageously, it is also possible, for example after use of the connector and of the complementary connector, to displace the connector relative to the complementary connector counter to the displacement direction, i.e. to displace the fluid conduit apertures counter to the displacement direction and thereby reduce and in particular prevent a flow of fluid between the connector and the complementary connector.

The expression "substantially plane" within the meaning of the invention signifies that the displacement surface is preferably a plane surface. The displacement surface can, however, deviate from an ideal plane surface in the geometric sense. In particular, the displacement surface is a plane surface in the context of manufacturing accuracy. Therefore, the term "substantially" within the meaning of the invention is in this connection synonymous for example with the term "in the context of manufacturing accuracy".

The term "sterile" is used in this invention with its customary meaning, that is to say, for example, free of microorganisms, aseptic, or infertile. Sterile, however, does not have to mean a complete absence of microorganisms or foreign bodies, but can imply a predetermined or predeterminable maximum number of microorganisms or foreign bodies. For example, the term "sterile" can signify a maximum number of microorganisms as is permitted or desired according to conventional industrial standards.

The connector preferably comprises a locking device which is arranged such that it can be moved along a locking direction in order to engage with a complementary locking device of the complementary connector, the locking direction being different than the displacement direction.

If, starting from a first predetermined position, the connector is displaced along the displacement direction relative to the complementary connector, the locking device is preferably configured in such a way as to prevent a displacement of the connector relative to the complementary connector beyond a second predetermined position. The first predetermined position is preferably a position of the connector relative to the complementary connector at which the engagement device of the connector and the complementary engagement device of the complementary connector have just come into engagement, i.e. the connector and the complementary connector are not yet displaced relative to one another. The second predetermined position is, for example, a position at which the fluid conduit apertures of the connector and of the complementary connector lie substantially opposite one another. In other words, the locking device can be designed to permit a displacement of the connector relative to the complementary connector only until a maximum flow of fluid is permitted from the connector to the complementary connector or a maximum flow of fluid is permitted from the complementary connector to the connector.

The locking device is preferably configured in such a way as to limit a displacement only in one direction, in particular along the displacement direction. However, the locking device can also be configured in such a way as to prevent a displacement of the connector relative to the complementary connector at preferably the predetermined second position both along and also counter to the locking direction. In other words, the connector and the complementary connector are preferably held at the second predetermined position, the locking device being configured in such a way that the locking of the connector to the complementary connector can be released again. For example, the connector can be locked to the complementary connector in such a way that the respective fluid conduit apertures lie substantially opposite one another, i.e. a maximum flow of fluid is permitted between the connector and the complementary connector. A movement of the connector relative to the complementary connector along and/or counter to the displacement direction is substantially prevented with the aid of the locking device, which is in engagement with the complementary locking device. If the connector and the complementary connector are to be separated from one another again, the locking of the locking device to the complementary locking device can be released, as a result of which the connector can be displaced relative to the complementary connector along or counter to the displacement direction. As a consequence, the respective fluid conduit apertures can also be displaced relative to one another, and a flow of fluid from the connector to the complementary connector or from the complementary connector to the connector can thus be restricted or prevented.

The locking device can, for example, have pins which are movable along the locking direction and which can engage in openings or recesses of the complementary locking device. However, the locking device can also comprise a projection which can abut against a shoulder of the complementary locking device, for example in order to prevent a further movement of the connector relative to the complementary connector along the locking direction.

Moreover, the locking device is preferably configured so as to be pretensioned counter to the locking direction.

In particular, it may be possible for the locking device to comprise a pin which is mounted to be displaceable along or counter to the locking direction. Furthermore, the locking device can, for example, comprise a spring element which deflects the pin along the locking direction. Instead of the spring element, another means can also be used that allows the pin to be moved along the locking direction. When the connector and the complementary connector are situated at a position where they are not intended to be locked, the pin is held in its position, for example by the displacement surface, counter to the force of the spring element. By contrast, when the connector and the complementary connector are situated at a position where they are intended to be locked to one another, the guide surface of the complementary connector can, for example, have a recess which allows the pin to move along the locking direction as a result of the force of the spring element, such that the pin protrudes into the recess of the guide surface. The recess of the guide surface is in this case a component part of the complementary locking device.

Therefore, the locking device is particularly preferably designed to engage automatically with the complementary locking device when the connector and the complementary connector are arranged in a locking position. The locking position is preferably a position of the connector relative to the complementary connector in which a flow of fluid, in particular a maximum flow of fluid, is permitted from the connector to the complementary connector and vice versa.

Moreover, the sterile cover preferably comprises a displaceable surface cover and/or a releasable edge cover.

The displaceable surface cover can, for example, be made from the same material as the connector, the displaceable surface cover being arranged substantially opposite the displacement surface, for example, and being displaceable along the displacement direction. The displaceable surface cover can, for example, cover the fluid conduit aperture, as a result of which in particular a flow of fluid through the fluid conduit aperture is prevented. The displaceable surface cover preferably covers the fluid conduit aperture in a sterile manner. The displaceable surface cover can, however, also be nonsterile, and an additional sterile element, for example a sterile film, can be arranged between the displacement surface and the displaceable surface cover, said additional sterile element covering or closing at least the fluid conduit aperture in a sterile manner.

The releasable edge cover can, for example, be a sterile film, in which case only the face directed toward the edge need be sterile. The sterile film can cover an edge and/or surface of the connector and also an edge and/or surface of the surface cover in a sterile manner.

The displaceable surface cover is preferably configured so as to fix the locking device along the locking direction.

In other words, a movement of the locking device along the locking direction is prevented by means of the surface cover. The locking device is pressed against the surface cover by means of a force of the spring element, i.e. the locking device is pretensioned, as a result of which the locking device is fixed releasably along the locking direction.

The term "fixed releasably" within the meaning of the invention signifies that the locking device is substantially immobilized or held at a predeterminable position. However, the locking device can also be moved along or counter to the locking direction, if for example the surface cover is removed from the locking device, i.e. there is no longer any contact between the locking device and the surface cover. In other words, the locking device is pretensioned in the locking direction counter to the spring force of the spring element by means of the surface cover.

It is possible, in particular, to arrange the locking device at least partially along or in the fluid conduit. Particularly preferably, the locking device can also be a component part of the fluid conduit.

Moreover, the releasable edge cover preferably covers, in a sterile manner, one end of the displaceable surface cover that comes into in contact with the complementary connector substantially with a form fit.

To put it another way, the engagement device can be a component part both of the connector and also of the displaceable surface cover. Therefore, the displaceable surface cover can, by means of the engagement device, engage with the complementary engagement device of the complementary connector. An edge or surface of the surface cover comes into contact with the engagement device, in particular with an edge or surface of the engagement device of the complementary connector, preferably with a form fit. The edge or surface of the surface cover is preferably covered in a sterile manner by the sterile edge cover.

The sterile edge cover preferably also covers an edge or a surface of the connector that engages with a complementary engagement device of the surface cover of the complementary connector. In particular, it is possible for the sterile edge cover to be configured in two parts, one part covering the edge or surface of the displaceable surface cover, and the other part covering the edge or surface of the connector. The sterile edge cover can also be designed in one piece and can cover the edge and/or surface of the surface cover in a sterile manner and also cover the corresponding edge and/or surface of the connector in a sterile manner. In other words, the sterile edge cover covers a surface or edge of the engagement device that comes into engagement with the surface or edge of the complementary engagement device of the complementary connector preferably with a form fit. Consequently, the releasable edge cover preferably covers at least one end of the connector that is designed to come into contact with an end of the surface cover of the complementary connector, in which case in particular the surface cover of the complementary connector is arranged to be displaceable along and/or counter to the displacement direction.

Moreover, the displaceable surface cover is preferably in planar contact with the displacement surface.

Consequently, the surface cover has a substantially plane contact surface corresponding to the displacement surface, said contact surface touching the displacement surface at least in some areas. The contact surface is, for example, configured so as to pretension or fix the locking device counter to the locking direction.

The fluid conduit is particularly preferably a component part of the locking device.

The locking device is preferably configured so as to provide a leaktight contact of the connector with the complementary connector.

The connector can also preferably be connected to a container in a leaktight manner.

The connector can in this case be connected directly to the container. In other words, the fluid conduit of the connector is connected directly to the container, preferably in a sterile manner. It is possible for the connector to be connected to the complementary connector with the aid of the coupling device, i.e. for an aperture of the fluid conduit to be connected preferably in a sterile manner to the fluid conduit of the complementary connector. A further aperture of the fluid conduit is connected to the container preferably in a sterile manner. The connection between the container and the connector can be made using a hose, for example. The connector can, for example, be arranged releasably on the container or can be connected to it.

Consequently, fluid can pass from the container, if appropriate by way of a hose, through the connector and the complementary connector and be transferred for example into a container attached to the complementary connector. However, the complementary connector can also be attached to the blood system of a living organism, for example a mammal, in particular a human, preferably by way of a hose or a hose system. In particular, the flow through the connector and/or the complementary connector can also take place in the opposite direction, i.e. starting from one container for example in this sequence, through the complementary connector, through the connector, and finally into the container connected to the connector. In other words, the container connected to the connector can be filled and/or emptied by means of flow of fluid through the connector.

The container is preferably a bioreactor, a bag or a filter housing, particularly preferably a filter capsule. The connection between the connector and the container is also preferably sterile.

Another aspect of the present invention is a connector system for leaktight connection of a fluid inlet of a connector to a fluid outlet of a complementary connector, the connector and the complementary connector each being configured as claimed in one of the preceding claims.

Moreover, a further aspect of the present invention concerns the method of use of a connector and of a complementary connector for sterile connection of a fluid inlet of the connector to a fluid outlet of the complementary connector, with the following steps:

making available a connector and a complementary connector in each case configured according to the invention, bringing the engagement device of the connector into engagement with the complementary engagement device of the complementary connector, and displacing the connector relative to the complementary connector along the displacement direction.

Particularly preferably, the method of use of a connector and of a complementary connector for sterile connection of a fluid inlet of the connector to a fluid outlet of the complementary connector comprises the following step:

locking the locking device of the connector to the complementary locking device of the complementary connector.

Preferably, prior to the step of locking the locking device of the connector to the complementary locking device of the complementary connector, a step is performed involving removing the sterile covers.

BRIEF DESCRIPTION OF THE DRAWINGS

Preferred embodiments of the present invention are described with reference to the examples in the following figures, in which.

DETAILED DESCRIPTION OF THE PREFERRED EMBODIMENTS

Figure 1:
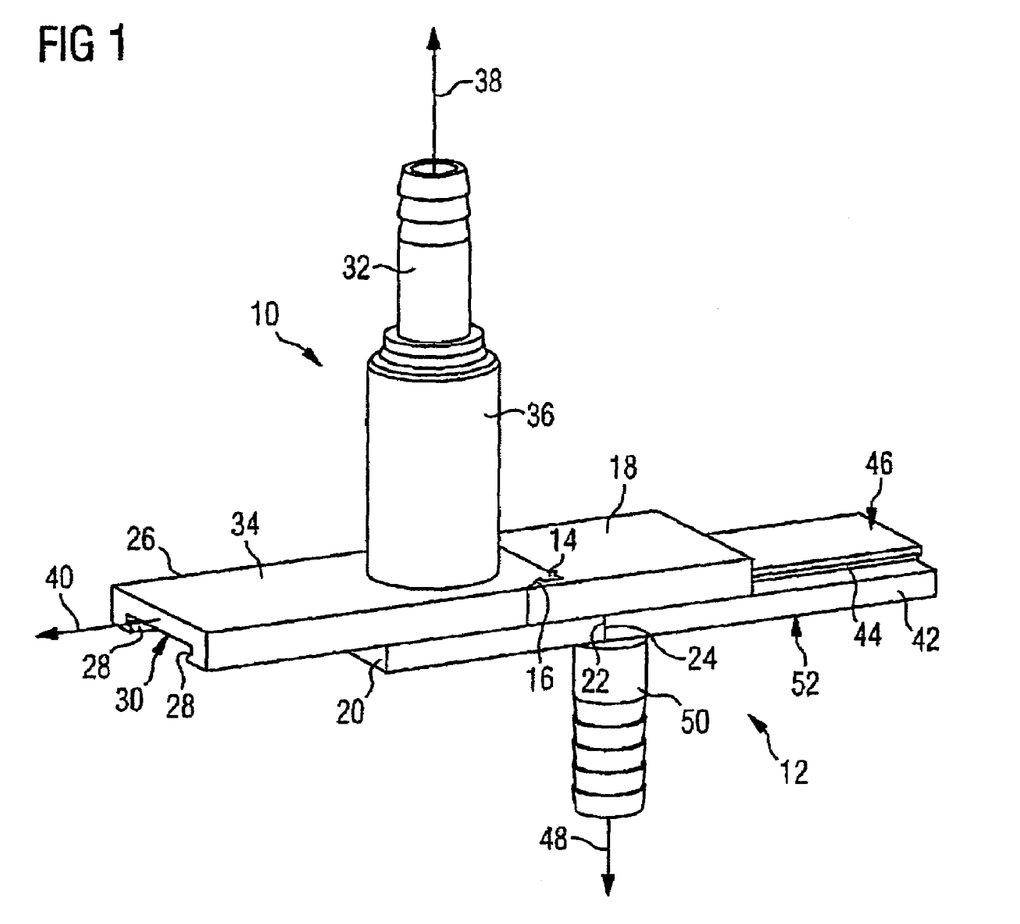
FIG. 1 shows a perspective schematic view of a system of a preferred connector with a preferred complementary connector.

FIG. 1 shows a connector 10 and complementary connector 12. The connector 10 is connected to the complementary connector 12 by means of an engagement device 14. In particular, the engagement device 14 is in engagement with a complementary engagement device 16 of a cover device 18 of the complementary connector 12. FIG. 1 also shows a cover device 20 of the connector 10, said cover device 20 engaging via an engagement device 22 with a complementary engagement device 24 of the complementary connector 12. The engagement device of the connector 10 is in two parts in the preferred embodiment shown in FIG. 1, comprising the engagement device 14 and the engagement device 22 of the cover device 20. Analogously, the engagement device of the complementary connector 12 is in two parts. The engagement device of the complementary connector 12 comprises the complementary engagement device 16 of the cover device 18 and the complementary engagement device 24.

The connector 10 also comprises a displacement device 26. The displacement device 26 has two guide walls 28 and a displacement surface 30. The guide walls 28 are inclined in relation to a normal direction of the displacement surface 30, i.e. the guide walls 28 are not perpendicular to the displacement surface 30. The connector 10 also has a fluid conduit in the form of a tube 32. The tube 32 is arranged substantially perpendicular to the displacement surface 30. However, the fluid conduit can also have another form and arrangement. A tube fastener 36 is also arranged on an outer face 34 of the displacement device 26. The tube fastener 36 surrounds the tube 32 along part of its extent in the longitudinal direction or an axial direction 38 of the tube 32. A fluid conduit aperture 60 (shown in FIG. 3) is also arranged in the displacement device 26. The tube fastener 36 is preferably arranged on the outer face 34 of the displacement device 26 in such a way that a center point of the preferably circular fluid conduit aperture coincides with a center point of the tube fastener 36. The displacement device 26 and the tube fastener 36 are particularly preferably produced in one piece. The tube fastener 36 can also be connected to the displacement device in a different way. For example, the tube fastener can be screwed onto the displacement device.

The cover device 20 is preferably arranged displaceably on the connector 10. In particular, the cover device 20 is arranged displaceably on the displacement device 26 of the connector 10. The cover device 20 can be displaced along a displacement direction 40. When the engagement device 22 of the cover device 20 is in engagement with the complementary engagement device 24 of the complementary connector 12, the cover device 20 and the complementary connector 12 can be displaced along the displacement direction 40.

FIG. 1 also shows a displacement device 42 of the complementary connector 12. The displacement device 42 of the complementary connector 12 has inclined, complementary guide walls 44 and a complementary displacement surface 46. The inclined guide walls 44 are preferably inclined relative to the complementary guide surface 46 at an angle different than 90°. Particularly preferably, the guide walls 28 of the displacement device 26 of the connector 10 and the corresponding complementary inclined guide walls 44 of the complementary displacement device 42 of the complementary connector 12 are arranged substantially parallel when the engagement devices 14, 22 are in engagement with the corresponding complementary engagement devices 16, 24. In such a position, the displacement surface 30 and the complementary displacement surface 46 are also substantially parallel. Particularly preferably, the inclined guide walls 28 engage with the corresponding complementary inclined guide walls 44 when the connector 10 and the complementary connector 12 are displaced relative to one another, i.e. the connector 10 can be held stationary and the complementary connector 12 can be displaced along the displacement direction 40. Alternatively, however, the complementary connector 12 can also be held stationary and the connector 10 can be displaced counter to the displacement direction 40. For example, it is also possible for the complementary connector 12 to be displaced along the displacement direction 40 and for the connector 10 at the same time to be displaced counter to the displacement direction 40.

When the displacement device 26 is in engagement via the engagement device 14 with the complementary engagement device 16 of the cover device 18, the connector 10 and the cover device 18 of the complementary connector 12 are displaceable with one another as a unit. Likewise, the complementary connector 12 and the cover device 20 of the connector 10 are displaceable with one another as a unit when the engagement device 22 of the cover device 20 and the complementary engagement device 24 of the complementary connector 12 are in engagement.

A movement of the cover device 20 relative to the displacement device 26 in a direction not substantially identical to the displacement direction 40 is not possible when the displacement device 26 and the cover device 20 are in engagement. Analogously, a movement of the cover device 18 relative to the complementary displacement device 42, in a direction different than the displacement direction 40, is not possible when the cover device 18 and the complementary displacement device 42 are in engagement. The same applies to the connector 10 and the complementary connector 12 when the displacement device 26 and the complementary displacement device 42 are in engagement.

The engagement devices 14, 22 and the complementary engagement devices 12, 24 are preferably configured in such a way that the connector and the complementary connector can be connected along an engagement direction (not shown). The engagement direction can, for example, be parallel to the displacement direction 40. However, the engagement direction can also be parallel to the axial direction 38.

When the engagement devices 14, 22 and the complementary engagement devices 16, 24 are in engagement, the connector 10 and the complementary connector 22 can be displaced parallel to the displacement direction 40 until the fluid conduit apertures (not shown) lie over one another. In other words, the connector 10 and the complementary connector 12 can be displaced until the axial direction 38 of the tube 32 and an axial direction 48 of a tube 50 of the complementary connector 12 are coincident with one another. The tube 50 is, for example, arranged on an outer face 52 of the complementary connector 12, the axial direction 48 being coincident with a center point of the fluid conduit aperture (not shown) of the complementary connector 12 or the displacement device 42 of the complementary connector 12. The tube 50 and the displacement device 42 can be produced in one piece for example, i.e. the complementary connector 12 can be produced in one piece for example.

As soon as the axial direction 38 of the tube 32 of the connector 10 and the axial direction 48 of the tube 50 of the complementary connector 12 lie coincident with one another, the connector 10 and complementary connector 12 are connected to one another such that a maximum flow of fluid through the tube 32 of the connector 10 into the tube 50 of the complementary connector 12 is possible, said connection of the tube 32 of the connector 10 to the tube 50 of the complementary connector 12 being leaktight to the outside. In other words, fluid located in the tube 32 can flow into the tube 50 but no fluid can escape outward through the area of contact of the two tubes 32, 50, i.e. to the environment. Likewise, foreign material from the environment cannot pass through the area of contact of the two tubes 10, 50 and into the interior of the tubes 10, 50.

Figure 2:
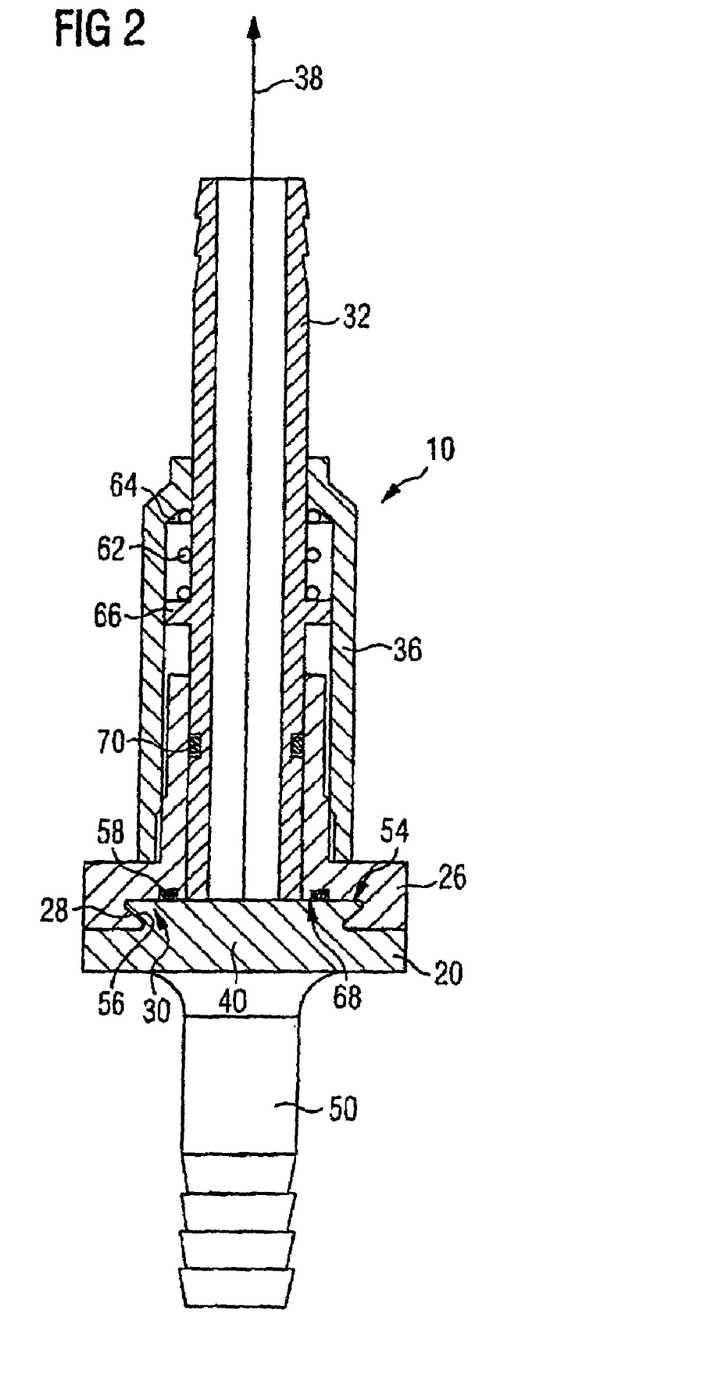
FIG. 2 shows a partial sectional view according to FIG. 1.

FIG. 2 shows a partial sectional representation of FIG. 1 along a section plane which is perpendicular to the displacement direction 40 and includes the axial direction 38. The sectional view in FIG. 2 shows a preferred embodiment of the connector 10 and a preferred embodiment of the complementary connector 12. In particular, the sectional view shows the tube 50 of the complementary connector 12 and the cover device 20 of the connector 10, said tube 50 not lying in the section plane. As shown in FIG. 1, the cover device 20 is connected to the complementary connector 12, in particular to the displacement device 42 of the complementary connector 12, by means of the engagement device 22 and the complementary engagement device 24. The displacement surface 30 of the displacement device 26 of the connector 10 is here in preferably planar contact with a displacement surface 54 of the cover device 20. Moreover, the cover device 20 has inclined guide walls 56. The guide walls 56 of the cover device 20 engage with the guide walls 28 of the displacement device 26 in such a way that the cover device 20 can be displaced along the displacement direction 40 relative to the connector 10. The cross section of the cover device 20 preferably has a substantially identical form to the displacement device 42 of the complementary connector 12. When the complementary connector 12 and the cover device 20 are connected to one another by means of the engagement device 22 and the complementary engagement device 24, the cover device 20 and the complementary connector 12 can be displaced with one another along or counter to the displacement direction 40 in order to permit a continuous flow of fluid.

FIG. 2 also shows a sealing means, for example in the form of an O-ring 58. The O-ring is preferably arranged in a depression in the displacement surface 30 such that the O-ring protrudes at least partially from the displacement surface 30. When the cover device 20 is arranged on the connector 10, in particular on the displacement device 26 of the connector 10, the O-ring 58 is preferably in press contact with the displacement surface 54 of the cover device 20. Moreover, the O-ring is preferably arranged centrally around the tube 32 or a fluid conduit aperture 60 of the displacement device 26. The O-ring 58 thus establishes a leaktight contact between the displacement device 26 and the cover device 20. If fluid is located in an inside of the tube 32, the fluid cannot escape from the connector 10 through the fluid conduit aperture 60. Likewise, foreign bodies from the environment cannot pass into the inside of the tube 32, i.e. contact between the environment and the fluid in the inside of the tube 32 is avoided.

FIG. 2 also shows a spring 62. The spring 62 is arranged in such a way that it presses at one end against a shoulder 64 of the tube attachment 36 and at the other end against a shoulder 66 of the tube 50. Consequently, the tube is pressed away from the shoulder 64 counter to the axial direction 38, as preferred locking direction. A movement of the tube is limited in particular by the displacement surface 54 of the cover device 20, which tube 32 projects into the fluid conduit aperture 60 and, preferably flush with a bottom edge 68 of the fluid conduit aperture 60, comes into contact with the displacement surface 54 of the cover device 20.

A further sealing element in the form of an O-ring 70 is also arranged on the tube 32. The O-ring is arranged in particular in a depression of the tube 32, the O-ring 70 establishing a leaktight connection between the displacement device 26 and the tube 32. In particular, the tube 32 can be moved along or counter to the axial direction 38 relative to the tube fastener 36 and the displacement device 26. If in particular the complementary condenser 12 is positioned relative to the connector such that the axial direction 38 of the tube 32 and the axial direction 48 of the tube 50 coincide with one another, the tube 32 is moved, by the spring force of the spring 62, counter to the axial direction 38, as preferred locking direction, toward the complementary connector 12, in which case the tube 32 passes completely through the fluid conduit aperture 60 and engages in an engagement aperture (not shown) of the complementary connector 12, in particular of the displacement device 42. The engagement aperture can, for example, be the fluid conduit aperture (not shown) of the complementary connector. A movement of the connector 10 relative to the complementary connector 12 along or counter to the displacement direction 40 is therefore prevented. The tube 32 consequently serves both as fluid conduit and also as locking device. Analogously, the tube 50 of the complementary connector 12 serves as fluid conduit, and an aperture (not shown) in the complementary displacement device 42 (not shown) serves as a complementary engagement device of the complementary connector 12. The locking device can, however, also be independent of the tube 32. It is thus possible, in particular, for the displacement device 26, the tube-fastening device 36 and the tube 32 to be produced in one piece. The locking device can, for example, be designed in the form of at least one pin which is arranged so as to be movable along the axial direction 38. The pin can, for example, be pressed counter to the axial direction 38 by way of a spring and can come into engagement with at least one aperture of the complementary connector 12, in particular in the complementary displacement surface 46 of the complementary displacement device 42, as a result of which a movement of the connector 10 relative to the complementary connector 12 along or counter to the displacement direction 40 is blocked. A movement of the connector 10 relative to the complementary connector 12 along or counter to the axial direction 38 is prevented by way of the inclined guide walls 28, 56 and the inclined complementary guide walls 44. Consequently, the connector 10 and the complementary connector 12 can be moved relative to one another, in and counter to the displacement direction 40, with the aid of the displacement device 26 and the complementary displacement device 42, and with the cover devices 18, 20 being moved with them at the same time. When the connector 10 and the complementary connector 12 are positioned relative to one another in such a way that a maximum flow of fluid through the tube 32 and the tube 50 is permitted, with sealing means, for example the O-ring 58, substantially preventing escape of fluid to the environment or contact between the fluid and the environment, the connector 10 and the complementary connector 12 are locked. A relative movement along or counter to the displacement direction 40 is then no longer possible. Consequently, a safe exchange of fluid between the tube 32 and the tube 50 is possible. In particular, the tube 32 can be connected to a container (not shown), for example by way of a hose (not shown) or directly, said container holding a fluid which, from the container, passes through the connector 10 and the complementary connector 12. Alternatively, however, the container can also be filled by delivery of fluid via the complementary connector 12 and the connector 10.

Moreover, the cover device 20 can also be arranged on the displacement device 26 of the connector 10 in such a way that the inside of the tube 32 is closed off in a sterile manner from the environment. The cover device 20 can also be arranged such that at least a partial area of the displacement surface 30 is closed off in a sterile manner from the environment, the cover device 20 being configured in particular in such a way that the fluid conduit aperture 60 is separated in a sterile manner from the environment or from a surrounding medium.

Alternatively, a further sterile cover (not shown), for example in the form of a sterile film, can be arranged between the guide wall 28 and the cover device 20, as a result of which the inside of the tube 32 or the fluid conduit aperture 60 is separated in a sterile manner from the environment. It is therefore not necessary for the cover device 20 to permit sterile covering of this kind. Instead, the cover device can be nonsterile, and the sterile film can close off the inside of the tube 32 or the fluid conduit aperture 60 in a sterile manner from the environment. The sterile film can also separate a partial area of the displacement surface 30 or the whole displacement surface 30 from the environment in a sterile manner or cover the displacement surface 30 in a completely sterile manner.

Figure 3:
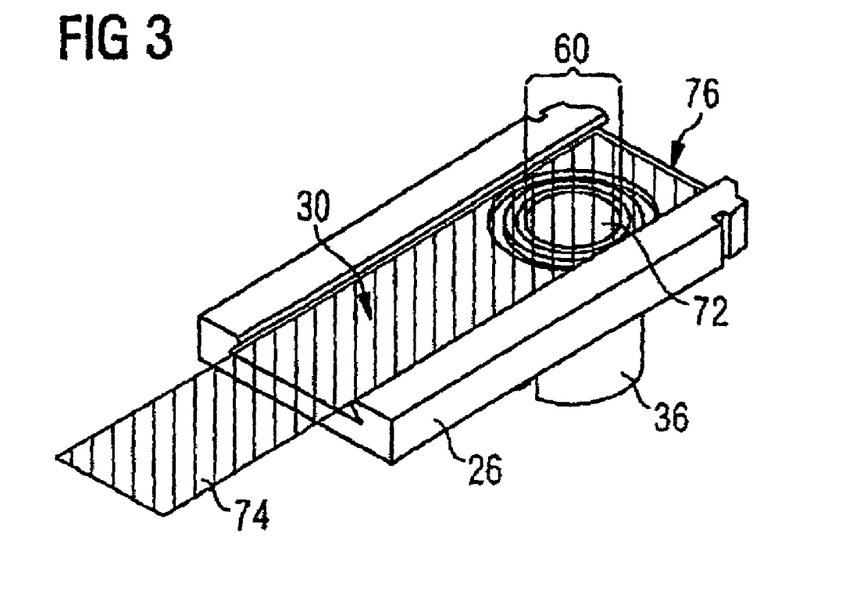
FIG. 3 shows a perspective schematic view of a preferred connector according to FIG. 1.

FIG. 3 shows the displacement device 26 and the tube fastener 36 of the connector 10. The fluid conduit aperture 60 is arranged in the displacement surface 30 of the displacement device 26. The fluid conduit aperture 60 is surrounded by a depression or circular ditch 72. The circular ditch 72 serves to receive the O-ring 58 (not shown). FIG. 3 also shows a sterile film 74. The sterile film covers a partial area of the displacement surface 30 of the displacement device 26 and also the fluid conduit aperture 60. Moreover, the sterile film 74 also covers the circular ditch 72. When the O-ring 58 is arranged in the circular ditch 72, the sterile film 74 also covers the O-ring 58. The tube 32 is not shown in FIG. 3. A surface 76 is also shown in FIG. 3. If, for example, the cover device 20 (not shown) is designed in such a way that the cover device 20 covers, in a sterile manner, the fluid conduit aperture and, if appropriate, the circular ditch 72 with the O-ring 58 arranged therein and, if appropriate, the area of the displacement surface 30, then the sterile film 74 can also be arranged only along the surface 76.

Figure 4:
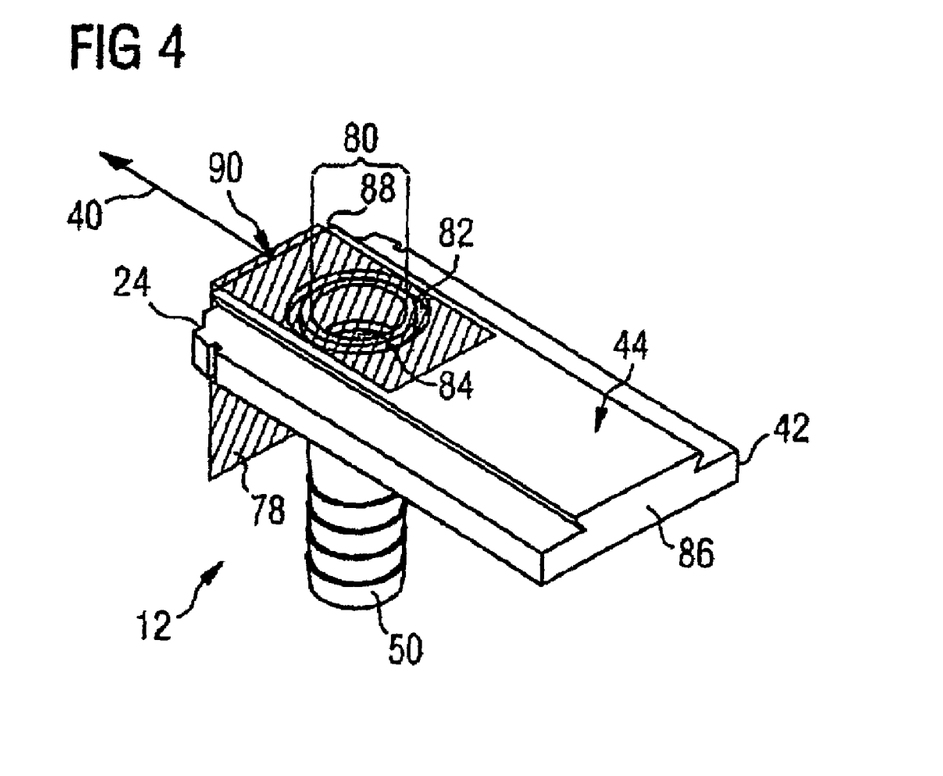
FIG. 4 shows a perspective schematic view of a preferred complementary connector according to FIG. 1.

FIG. 4 shows the complementary connector 12. A sterile film 78 is arranged on the complementary connector 12. The sterile film 78 covers a fluid conduit aperture 80 of the complementary connector 12. In particular, the fluid conduit aperture 80 corresponds to an inside of the tube 50. The complementary displacement device 42, the tube 50 and the fluid aperture 80 are particularly preferably designed in one piece. Moreover, the fluid conduit aperture 80 is surrounded by a circular ditch 82. The circular ditch 82 is in particular designed to receive a sealing means, for example an O-ring (not shown). FIG. 3 also shows a shoulder 84 arranged in the inside of the tube 50. When the connector 10 (not shown) and the complementary connector 12 are positioned in such a way that a maximum flow of fluid is permitted from the tube 32 of the connector 10 into the tube 50, the tube 32 is pressed counter to the axial direction 38, by virtue of the spring force of the spring 62, and engages with the inside of the tube 50. In particular, a bottom edge of the tube 32 strikes against the shoulder 84, as a result of which a further movement of the tube 32 counter to the axial direction 38 is blocked. Consequently, a movement of the connector 10 relative to the complementary connector 12 along or counter to the displacement direction 40 is prevented. In this position, the O-ring (not shown) which is arranged in the circular ditch 82, and the O-ring 58 which is arranged in the circular ditch 72, can for example also make contact with each other, thus preventing an escape of fluid from the inside of the tube 32 or from the inside of the tube 50 or from the fluid conduit apertures 60, 80 to the environment. Likewise, foreign material cannot get into the inside of the tubes 32, 50 or of the fluid conduit apertures 60, 80.

As shown in FIG. 2, the sterile film 78 can be substantially a plane film which is arranged along the complementary guide wall 44 and protrudes beyond an end 86 of the complementary guide wall 44, the end 86 lying remote from the engagement device 24. However, as is also shown in FIG. 4, the sterile film 78 can also be bent about an edge 88 and at least partially cover a surface 90, in which case the sterile film 78 protrudes beyond the complementary displacement device 42. The edge 88 and the surface 90 are arranged at an edge of the complementary connector at which the complementary engagement device 24 is arranged. If the cover device 20 (shown in FIG. 1 and FIG. 2) is arranged on the complementary displacement device 42, the sterile film 78 is thus situated between the cover device 20 and the complementary displacement device 42.

The connector 10 can consequently be coupled to the complementary connector 12 in such a way that the engagement device 14 is brought into engagement with the complementary engagement device 16 (of the cover device 18) of the complementary connector 12. At the same time, the engagement device 22 (of the cover device 20) of the connector 10 is also brought into engagement with the complementary engagement device 24 of the complementary connector 12, the sterile film 74 being arranged between the cover 20 and the connector 10, and the sterile film 78 being arranged between the cover device 18 and the complementary connector 12. The sterile film 74 is also arranged in such a way that it is folded about an edge of the connector 10 and is situated between the connector 10 and the cover device 18 of the complementary connector 12. The sterile film 74 therefore protrudes, substantially parallel to the axial direction 38, between the connector 10 and the cover device 18 of the complementary connector 12.

Analogously, the sterile film 78 is arranged between the complementary connector 12 and the cover device 18, the film being folded about the edge 88. The sterile film 78 is also arranged between the cover device 20 of the connector 10 and the complementary displacement device 42 of the complementary connector 12 such that the sterile film 78 protrudes, substantially parallel to the axial direction 48 of the tube 50, between the cover device 20 and the complementary connector 12. The connector 10 and the complementary connector 12 can be displaced relative to one another along the displacement direction 40 until, for example, the tube 32 comes into engagement with the tube 50 and a further movement along or counter to the displacement direction 40 is prevented. The tube 32 can in this case extend through the sterile films 74, 78. Alternatively, however, the sterile film 74 and the sterile film 78 can be removed, prior to displacement of the connector 10 relative to the complementary connector 12, by pulling on the protruding ends of the sterile film 74 and sterile film 78.

When the connector 10 and the complementary connector 12 are in a locked state that permits a flow of fluid through the tubes 32, 50 and the fluid conduit apertures 60, 80, the cover devices 18, 20 can be removed.

In order to release the connector 10 from the complementary connector 12, the covers 18, 20 can be arranged again on the complementary connector 12 and connector 10, respectively, and brought into engagement with the connector 10 and complementary connector 12, respectively. The connector 10 and the complementary connector 12 can then be displaced relative to one another counter to the displacement direction 40, the cover devices 18, 20 preventing an escape of fluid from the complementary connector 12 and the connector 10. For example, an exchange of fluid with containers that are attached to the connector 10 and complementary connector 12 can therefore be permitted and also interrupted, avoiding an escape of fluid to the environment or contact between the fluid and the environment.

Figure 5:
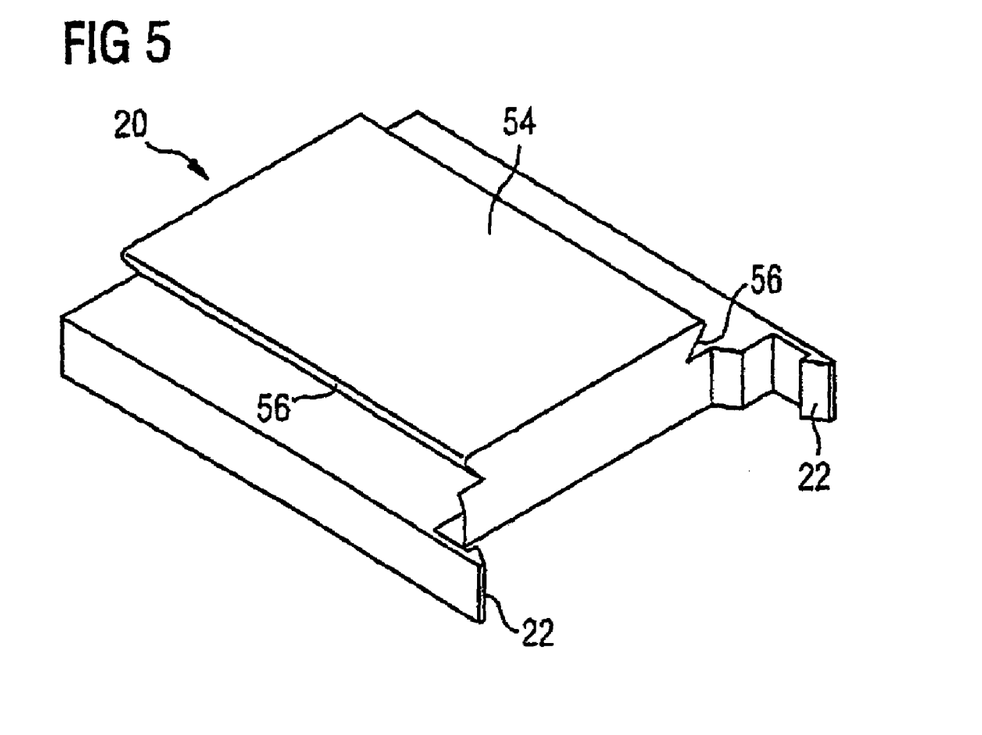
FIG. 5 shows a perspective schematic view of a preferred cover device according to FIG. 1.

FIG. 5 shows the cover device 20 of the connector 10 (not shown). The cover device 20 comprises the displacement surface 54 and also the inclined guide walls 56. FIG. 5 also shows the engagement device 22 of the cover device 20. The engagement device 22 is designed to come into engagement with the complementary engagement device 24 (not shown) of the complementary connector 12.

Figure 6:
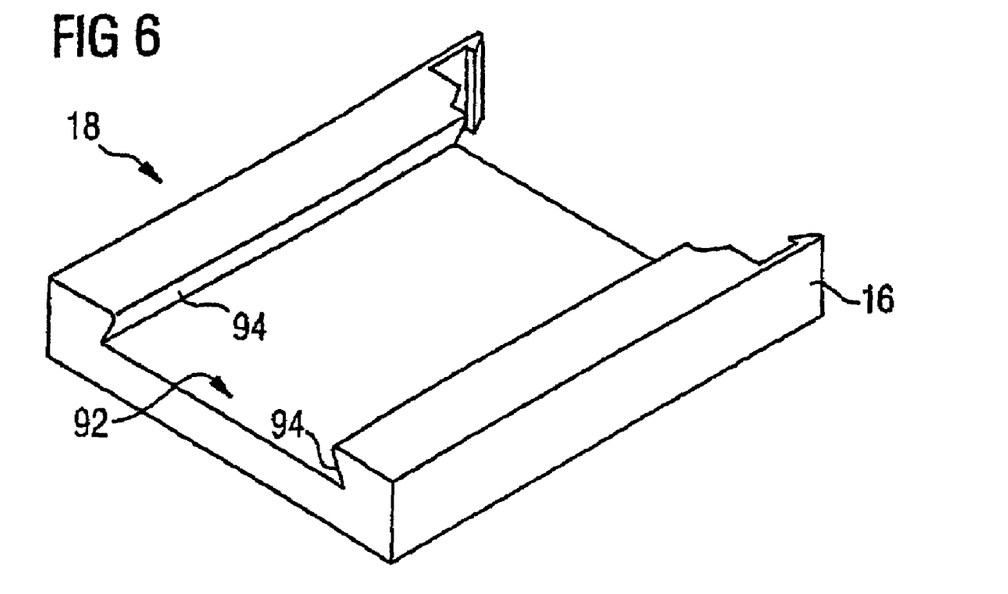
FIG. 6 shows a perspective schematic view of a further preferred cover device according to FIG. 1.

FIG. 6 shows the cover device 18 of the complementary connector 12 (not shown). The cover device 18 comprises a displacement surface 92 and also inclined guide walls 94. FIG. 6 also shows the complementary engagement device 16 which can be brought into engagement with the engagement device 14 of the connector 10 (not shown).

The present invention is not limited to the preferred embodiments described above. Instead, a connector according to the present invention can also deviate from the above preferred embodiments. For example, the connector and the complementary connector can be of identical configuration. In other words, the complementary connector can be designated as connector, and the connector as complementary connector. Moreover, the cover device of the connector or of the complementary connector can be designed in more than one piece, for example in two pieces, as is also shown for example in FIGS. 1 and 6.

The engagement device can deviate from the preferred engagement device indicated in the above description. For example, the engagement device can comprise a screw device. Moreover, the locking device can deviate from the above preferred embodiment. The locking device can, for example, be arranged independently of the tube.

List of Reference Numbers 10 connector
12 complementary connector
14 engagement device
16 complementary engagement device
18 cover device
20 cover device
22 engagement device
24 complementary engagement device
26 displacement device
28 guide wall
30 displacement surface
32 tube
34 outer face
36 tube fastener
38 axial direction, locking direction
40 displacement direction
42 complementary displacement device
44 complementary guide wall
46 complementary displacement surface
48 axial direction
50 tube
52 outer face
54 displacement surface
56 guide wall
58 O-ring
60 fluid conduit aperture
62 spring
64 shoulder
66 shoulder
68 bottom edge
70 O-ring
72 circular ditch
74 sterile film
76 surface
78 sterile film
80 fluid conduit aperture
82 circular ditch
84 shoulder
86 end
88 edge
90 surface
92 displacement surface
94 guide wall

What is claimed is:

1. A connector system for producing a sterile connection between a fluid inlet of a connector and the fluid inlet of a complementary connector comprising:
    a fluid conduit of the connector having a longitudinal axis therein;
    an engagement device of the connector designed to engage with a complementary engagement device of the complementary connector;
    a displacement device with a substantially plane displacement surface and a fluid conduit aperture which extends through the displacement surface and is connected to the fluid conduit of the connector, the fluid conduit being arranged substantially perpendicular to the displacement surface, the displacement device being designed to displace the connector and the complementary connector relative to one another in a displacement direction after the engagement device has engaged with the complementary engagement device, said displacement direction being substantially parallel to the displacement surface and perpendicular to the longitudinal axis of the fluid conduit; and
    a sterile cover device arranged displaceably on the displacement device and connected to the complementary connector, the sterile cover device designed to cover at least the fluid conduit aperture in a sterile manner, wherein, in a first position of the displacement device, the fluid conduit of the connector aligns with the fluid outlet of the complementary connector and, in a second position of the displacement device, the fluid conduit of the connector aligns with the sterile cover device to prevent flow of fluid between the connector and the complementary connector,
    wherein the fluid conduit is movable along the longitudinal axis and pretensioned in a locking direction toward the complementary connector to engage complementary locking device of the complementary connector to prevent movement of the connector relative to the complementary connector when the connector and the complementary connector are arranged in the first position and to engage the sterile cover device to prevent movement of the fluid conduit along the longitudinal axis at the second position, wherein a spring biases the fluid conduit in the locking direction without external input such that a bottom edge of the fluid conduit is positioned on a shoulder of the complementary connector at the first position, and further wherein force of the spring is capable of being overcome by axial movement of the fluid conduit when the displacement device is moved from the first position to the second position.

2. The connector system as in claim 1, wherein the sterile cover device comprises a displaceable surface cover and/or a releasable edge cover.

3. The connector system as in claim 2, wherein the releasable edge cover covers, in a sterile manner, one end of the displaceable surface cover that comes into contact with the complementary connector substantially with a form fit.

4. The connector system as in claim 2, wherein the releasable edge cover covers one end of the connector that is designed to come into contact with an end of a surface cover of the complementary connector.

5. The connector system as in claim 2, wherein the displaceable surface cover is in planar contact with the displacement surface.

6. The connector system as in claim 2, wherein the fluid conduit is designed to ensure leaktight contact of the connector to the complementary connector.

7. The connector system as in claim 1, wherein the connector can be connected to a contained in a leaktight manner.

8. The connector system of claim 1 wherein the sterile cover device is removable at the first position.

9. The connector system of claim 8 wherein the sterile cover device is repositionable to enable displacement of the fluid conduit from the first position to the second position.

10. The method of use of a connector (10) and of a complementary connector (12) for sterile connection of a fluid inlet of the connector (10) to a fluid outlet of the complementary connector (12), comprising the steps of: making ready a connector (10) and a complementary connector (12) in each case configured as in claim 1; bringing the engagement device (14, 22) of the connector (10) into engagement with the complementary engagement device (16, 24) of the complementary connector (12); and displacing the connector (10) relative to the complementary connector (12) along the displacement direction (40).

11. The method of use of a connector (10) and of a complementary connector (12) for sterile connection of a fluid inlet of the connector (10) to a fluid outlet of the complementary connector (12) as in claim 10, with the further step: locking the fluid conduit (32) of the connector (10) to the complementary locking device (50, 80) of the complementary connector (12).

12. The method of use of the connector (10) and of the complementary connector (12) for sterile connection of a fluid inlet of the connector (10) to a fluid outlet of the complementary connector (12) as claimed in claim 10, wherein, prior to the step of locking the fluid conduit (32) of the connector (10) to the complementary locking device (50, 80) of the complementary connector (12), a step is performed involving removing the sterile covers (18, 20, 74, 78).

13. A connector system comprising:
- a tube defining a fluid conduit therein, the fluid conduit extending along a longitudinal axis;
- a shoulder extending from the tube external from the fluid conduit in a direction substantially perpendicular to the longitudinal axis;
- a tube fastener surrounding at least a portion of the tube about the longitudinal axis, the tube fastener having a shoulder extending in a direction at least partially perpendicular to the longitudinal axis;
- an engagement device displaceably engaged the tube, the tube moveable with respect to the engagement device in a direction substantially perpendicular to the longitudinal axis from a first position to a second position, the engagement device designed to cover one end of the fluid conduit at the first position to prevent flow from the fluid conduit, the first connector aligning with an aperture of the engagement device at the second position to permit fluid flow; and
- a spring positioned between the shoulder of the tube and the shoulder of the tube fastener to bias the tube in a direction of the longitudinal axis such that the tube extends within the aperture of the displacement device at the second position.

14. The connector system of claim 13, further comprising a complementary engagement device connected to the tube and displaceably engage with the engagement device.

15. the connector system of claim 14, wherein the engagement device has a first guide wall that engages a second guide wall of the complementary engagement device.

* * * * *